United States Patent [19]

Lowman

[11] 4,071,031

[45] Jan. 31, 1978

[54] INFLATABLE LEG ELEVATOR WITH MEANS FOR APPLYING THERMAL TREATMENT

[76] Inventor: Thomas Lowman, 455 Shore Acres Road, Arnold, Md. 21012

[21] Appl. No.: 718,480

[22] Filed: Aug. 30, 1976

[51] Int. Cl.² .............................................. A61F 7/00
[52] U.S. Cl. .................................. 128/402; 5/327 R;
128/89 R; 128/403; 128/DIG. 20
[58] Field of Search ................. 5/92, 327 R, 337, 338,
5/341; 128/89 R, 362, 399, 402, 403, DIG. 20

[56] References Cited

U.S. PATENT DOCUMENTS

| | | | |
|---|---|---|---|
| 1,950,571 | 3/1934 | Rubin | 5/337 |
| 2,612,645 | 10/1952 | Boland | 5/341 |
| 3,644,949 | 2/1972 | Diamond | 5/338 |
| 3,946,451 | 3/1976 | Spann | 5/327 R |

Primary Examiner—Robert W. Michell
Assistant Examiner—Jerome D. Stremcha
Attorney, Agent, or Firm—Bacon & Thomas

[57] ABSTRACT

The invention comprises a limb support having upper, middle and lower sections. The upper section includes two compartments for receiving a fluid or ice and forming a trough to receive a limb of the patient. The middle section is in the form of an inflatable compartment for adjusting the height of the unit. The lower section includes three triangular-shaped compartments for adjusting the angle at which the unit is to be rested.

6 Claims, 1 Drawing Figure

U.S. Patent
Jan. 31, 1978
4,071,031
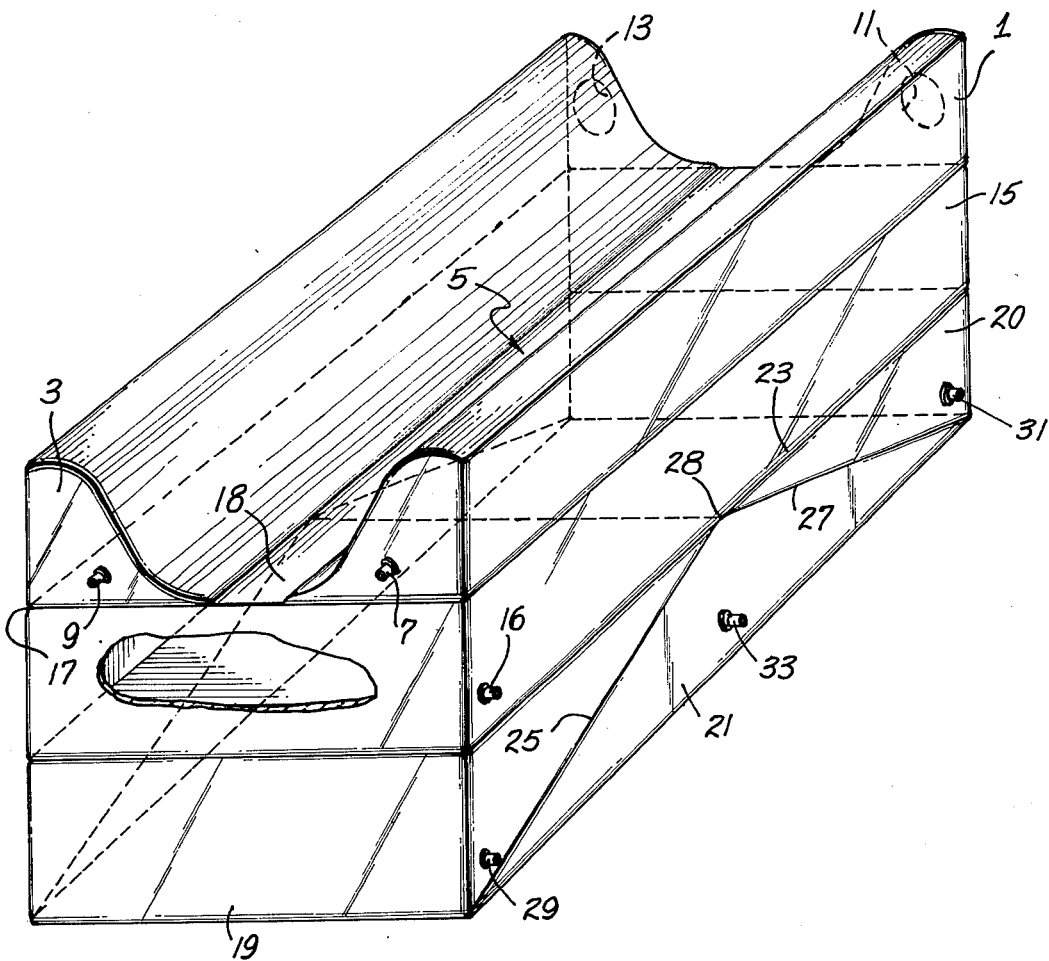

INFLATABLE LEG ELEVATOR WITH MEANS FOR APPLYING THERMAL TREATMENT

BACKGROUND

The invention relates to inflatable supports, and more particularly to an inflatable limb elevator, having an adjustable angle and height, and wherein the support can be utilized to apply thermal treatment to the limb being elevated.

Inflatable backrests, splints and even small seats for children are well known in the arts. Further, to put hot or cold liquids or even ice in splints, wraps and bandages is well known. Such devices are shown, for example, in U.S. Pat. Nos. 2,832,336; 3,628,537; 3,717,145 and 3,901,225.

More often, the method of elevating legs, for example, is by means of pillows. When it is necessary to add hot or cold compresses, it is usually done by means of towels soaked in very hot or ice cold water. These have the obvious disadvantage of wetting the pillows, bed linens and the like. Further, since they are exposed to the air, the compresses rapidly come to room temperature. Also, it is cumbersome to put the patient's leg in the proper position and have it remain there, with or without the application of heat or cold.

Even with the use of splints, bandages or wraps as illustrated in the prior art referred to above, there remains the problems of positioning the leg at a proper height and angle.

Thus, there has been a need for an inflatable leg elevator which can be adjusted to a desired angle, remain in the same location and apply thermal treatments to the leg.

OBJECTS AND SUMMARY

An object of the instant invention is to provide an inflatable leg elevator which can be adjusted relative to height and angle.

Another object is to provide an inflatable leg support which has means for the insertion of cold water or ice or hot water to provide a thermal treatment.

A further object is to provide a device which will be able to remain in relatively the same position when ice is inserted and at such time as when the ice melts.

Another object is to provide means for applying cold or heat to an injured leg or the like without putting any added weight or pressure on the limb.

Still another object is to provide a device which can be adjustable easily by either the patient, attendant or medical personnel.

Another object is to provide an inflatable support and/or heat applying device which is easily stored in an empty and deflated condition.

The invention comprises a limb support having upper, middle and lower sections. The upper section includes two compartments for receiving a fluid or ice and forming a trough to receive a limb of the patient. The middle section is in the form of an inflatable compartment for adjusting the height of the unit. The lower section includes three triangular-shaped compartments for adjusting the angle at which the unit is to be rested.

BRIEF DESCRIPTION OF THE DRAWING

The foregoing and other objects, features and advantages of the invention will become more apparent from the following detailed description and accompanying drawing, wherein the single FIGURE illustrates a perspective view of the leg elevator according to one form of the invention.

DETAILED DESCRIPTION OF THE INVENTION

As seen in the FIGURE, an inflatable leg elevator according to the invention is seen having a generally rectangular shape and being divided into several distinct, separate and unconnected compartments forming three sections. The first section includes a pair of upper compartments 1 and 3, forming a trough 5 to receive a leg or other limb. The size of the unit can obviously be modified for the particular limb and age of the patient.

The trough 5 with its rounded center portion is formed by a pair of compartments 1 and 3, inflatable by means of respective fluid-tight plugs or valves 7 and 9. Air can be blown into the valve openings 7 and 9 or water of a desired temperature can be inserted to provide hot or cold treatments. A pair of larger fluid-tight capped openings 11 and 13 are positioned in one end of compartments 1 and 3. Obviously, the caps can be located in some other position in the compartments 1 and 3. The caps are of sufficient size to permit the insertion of ice cubes for the purpose of cold treatments.

A center section or compartment 15 is seen with an air valve or plug 16 similar to plugs 7 and 9 above. The prime purpose of the center chamber, as will be seen below, is to regulate the height of the leg elevator. Center section 15 can be formed by the bottom wall 17 of compartments 1 and 3. Also the bottom of trough 5 can be secured to the top of the center section at 18.

The bottom section is divided into three compartments 19, 20 and 21. Compartments 19 and 20 are separated from the center section 15 by a layer of impermeable material 23; while compartments 19–21 are divided by inclined walls 25 and 27 having an apex 28 substantially in the center of the length of the support. The walls of the unit are made completely of air and water impermeable material such as polyvinylchloride, polyethylene or the like. The edges may be heat-sealed together to form the unit in the usual manner.

Compartment 19 has a plug-type valve 29 therein; compartment 20, a plug valve 31; and compartment 21, a plug valve 33.

The purpose of the three compartment lower section is for adjusting the angle of elevation to conform with the desired position of the limb and to conform with the particular angle to which a bed, chair or the like has been adjusted. By regulating the air in compartments 19, 20 and 21, the particular angle at which the unit will rest can be adjusted. Also, depending upon the amount of air in, for example, compartment 15, as well as the lower compartments, the firmness of the device can be regulated.

Hot or cold water or ice can be inserted via openings 11 and 13 in compartments 1 and 3 without applying undue pressure on the limb. Further, once the device is adjusted by the inflation of various compartments, the unit will remain stable, assuring the user that it will not slip, thus always maintaining hot or cold treatments in the desired location.

If both legs are to be elevated simultaneously, two units can be placed side-by-side, or a single unit with two troughs 5 can be constructed. The center compartments of a single, two trough unit may be connected together, depending upon whether or not it is desired that both legs be at the same angle and height. The middle and lower sections may likewise be interconnected.

While one embodiment of the invention has been described, it will be understood that it is capable of many further modifications and this application is intended to cover any variations, uses, or adaptions of the invention following in general, the principles of the invention and including such departures from the present disclosure as come within knowledge or customary practice in the art to which the invention pertains, and as may be applied to the essential features hereinbefore set forth and fall within the scope of the invention or the limits of the appended claims.

I claim:

1. A body limb elevator and support comprising:
   a. a plurality of air and water-tight sections in the form of compartments made of flexible material and being sealed from each other;
   b. the support including an upper section and a lower section;
   c. said upper section having a trough formed therein;
   d. said lower section having upper and lower substantially parallel walls and being divided into at least two separate compartments;
   e. means for inserting fluid into said at least two separate compartments;
   f. said at least two separate compartments being formed substantially triangular in cross-section, a wall between two of said at least two separate compartments being inclined upwardly from said lower wall of the support and contacting a compartment thereabove;
   whereby when one of said separate compartments has fluid therein and another of said separate compartments is substantially free of fluid, the support and trough will tilt; and when all of said separate compartments are substantially full of fluid the support will be substantially horizontal.

2. A body limb elevator as defined in claim 1 wherein said fluid is air, whereby said compartments are inflated.

3. A body limb elevator as defined in claim 1 wherein said at least one upper section includes at least one relatively large opening therein for the insertion of ice or the like.

4. A body limb elevator and support comprising:
   a. a plurality of air and water-tight sections in the form of compartments made of flexible material and being sealed from each other;
   b. the support including at least an upper section and a lower section;
   c. said upper section having a trough formed therein;
   d. said lower section being divided into three separate compartments;
   e. said three separate compartments being formed with triangular cross-sections;
   f. wherein one of said three compartments has a bottom extending substantially the length and width of the support and having a pair of inclined walls having an apex substantially in the center of the length of the support, said inclined walls forming a wall of the other two of said three compartments; and
   g. means for inserting a fluid in at least some of said compartments.

5. A body limb elevator and support comprising:
   a. a plurality of air and water-tight sections in the form of compartments made of flexible material and being sealed from each other;
   b. the support including at least an upper section and a lower section;
   c. said upper section including a pair of compartments forming a trough therein;
   d. said lower section including three compartments having triangular cross-sections;
   e. a third section being a middle section between said upper and lower sections and being in the form of a single compartment; and
   f. means for inserting a fluid in at least some of said compartments.

6. A body limb elevator as defined in claim 5 wherein the bottom of said trough abuts against the top of said middle section, and one of said three compartments having a bottom extending substantially the length and width of the support and including a pair of inclined walls having an apex substantially in the center of the length of the support, said inclined walls forming a wall of the other two of said three compartments, and the bottom of said middle section forming another wall of said other two compartments.

* * * * *